(12) United States Patent
Faller et al.

(10) Patent No.: US 7,892,220 B2
(45) Date of Patent: Feb. 22, 2011

(54) USE OF AN ADHESIVE AS AN INTESTINAL BARRIER FOR BARIATRICS

(75) Inventors: Craig N. Faller, Milford, OH (US); Bennie Thompson, Cincinnati, OH (US); Wells D. Haberstich, Loveland, OH (US); Anil K. Nalagatla, Mason, OH (US); Douglas J. Turner, Cincinnati, OH (US); Donna L. Korvick, Maineville, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 356 days.

(21) Appl. No.: 11/538,559

(22) Filed: Oct. 4, 2006

(65) Prior Publication Data
US 2008/0269715 A1   Oct. 30, 2008

(51) Int. Cl.
*A61M 31/00* (2006.01)
*A61F 2/00* (2006.01)
*A61F 2/02* (2006.01)

(52) U.S. Cl. .............. 604/506; 600/29; 623/23.65
(58) Field of Classification Search ... 604/890.1–892.1, 604/151–155; 623/23.64–23.66
See application file for complete search history.

(56) References Cited

U.S. PATENT DOCUMENTS

| | | | |
|---|---|---|---|
| 6,494,896 B1* | 12/2002 | D'Alessio et al. | 606/213 |
| 7,044,979 B2* | 5/2006 | Silverman et al. | 623/23.65 |
| 7,056,277 B2* | 6/2006 | Silverman et al. | 600/29 |
| 2005/0171556 A1* | 8/2005 | Murphy | 606/108 |
| 2008/0195225 A1* | 8/2008 | Silverman et al. | 623/23.65 |
| 2008/0234834 A1* | 9/2008 | Meade et al. | 623/23.65 |

* cited by examiner

*Primary Examiner*—Kevin C Sirmons
*Assistant Examiner*—Imani Hayman (57) ABSTRACT

An apparatus for achieving weight loss in a patient is disclosed. The apparatus has a barrier material and an applicator for dispensing the barrier material about the intestine. An injector is used to place the barrier material to block nutrient transfer from the intestine into the blood stream. The barrier material is a polymerizable adhesive that can be injected interstitially between layers of the intestine, or injected into vascular structures to partially block the flow of blood to the nutrient absorbing layers.

7 Claims, 6 Drawing Sheets

USE OF AN ADHESIVE AS AN INTESTINAL BARRIER FOR BARIATRICS

FIELD OF THE INVENTION

The present invention relates, in general, to bariatric surgery devices, and to apparatus and methods for reducing nutrient absorption in the gastric tract.

BACKGROUND OF THE INVENTION

Obese patients can have increased morbidity from excess weight. Extra weight can place strain on body circulatory systems, respiratory systems, the digestive system, and can stress or overload body organs. This can cause numerous medical conditions such as diabetes, high blood pressure, high cholesterol, sleep apnea, and can increase the risk of a major coronary event. Bariatric medicine is focussed on the prevention, control, and treatment of obesity. Diet, drugs, and surgery are the most common tools used to reduce a patient's calloric intake, reduce their weight, and save their lives.

Bariatric surgical techniques can result in dramatic weight loss for the morbidly obese and can add years to a patient's life. These surgeries can include stomach stapling to create a small pouch, intestinal bypass surgery, gastric banding, placement of a large filler object in the stomach to reduce the internal volume of stomach, and gastric sleeves.

The small intestine is attached to the pyloric valve at the base of the stomach. The pyloric valve regulates the passage of partially digested food from the stomach and into the first portion of the small intestine. The first foot and a half to two feet of the small intestine absorbs the majority of the nutrients from the partially digested food as it passes through. Intestinal bypass surgery is focussed on bypassing this section of the intestine with surgical cutting and stapling procedures such as a Roux-en-Y.

Malabsorptive surgical procedures block the absorption of nutrients or block the flow of nutrients to the blood stream. These procedures can require less radical surgery than a bypass, and can include implantable devices such as a gastric sleeve that is attached to the stomach or intestinal wall near the pyloric valve. The gastric sleeve extends down into the upper section of the small intestine and places a barrier between the partially digested food and the duodenum or nutrient absorbing section of the small intestine. This barrier reduces the amount of nutrients absorbed by the body and results in weight loss. U.S. Pat. No. 7,037,344 by Kagan et al. teaches a gastric sleeve apparatus, methods of attachment to the body, and methods of use in the treatment of morbid obesity.

As an alternate to gastric sleeves, other barrier materials or techniques could be used. For example, a fluid, or a semi-fluid (gel) could be used as a barrier if it could be restrained in position to block nutrient absorption. The fluid or semi-fluid barrier material could undergo a phase change such as from a liquid to a solid or to a semi-solid. Monomer and polymer adhesives such as the cyanoacrylates are initially fluid, adhere well to tissue, and can create a barrier to nutrient absorption in the intestines. Closure Medical has developed a 2-octyl cyanoacrylate compound with a long carbon chain (eight carbons) that is biocompatible, has good bonding strength, and has received FDA approval for topical use. Additional FDA clinical trials are underway to use cyanoacrylate adhesives for internal surgical use. These adhesives can be biocompatible, rigid or flexible, and biodegradable or non-biodegradable inside the body.

Consequently, a significant need exists for an effective barrier that can block nutrient intake to achieve weight loss in a patient, be easy to apply, can be placed with a minimally invasive procedure such as placement through in a natural body orifice, minimize patient recovery time, and result in lower surgical costs.

BRIEF SUMMARY OF THE INVENTION

The invention overcomes the above-noted and other deficiencies of the prior art by providing a surgical apparatus for achieving weight loss in a patient. The surgical apparatus comprises a polymerizable barrier material for reducing a transfer of nutrients from an organ to the bloodstream and a pump for dispensing the polymerizable barrier material. An applicator is provided for applying the dispensed polymerizable barrier material to an organ of the patient.

Also in accordance with the present invention, there is provided a method for placing a barrier in a nutrient absorbing organ to achieve weight loss in a patient. The method comprises first placing an applicator into or on the surface tissue of the nutrient absorbing organ. Next, a polymerizable fluid barrier is applied from the applicator to tissue at a site. The polymerizable fluid barrier reduces the transfer of nutrients from the nutrient absorbing organ into a patients blood stream.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive In bariatric surgery, it is desired to reduce an obese patients weight by one or more of diet, exercise, drugs, or surgery. A variety of bariatric surgical techniques are available to those skilled in the art, including placement of a barrier in or around the intestines that can reduce or eliminate the absorption of nutrients through the intestinal wall.

Figure 1:
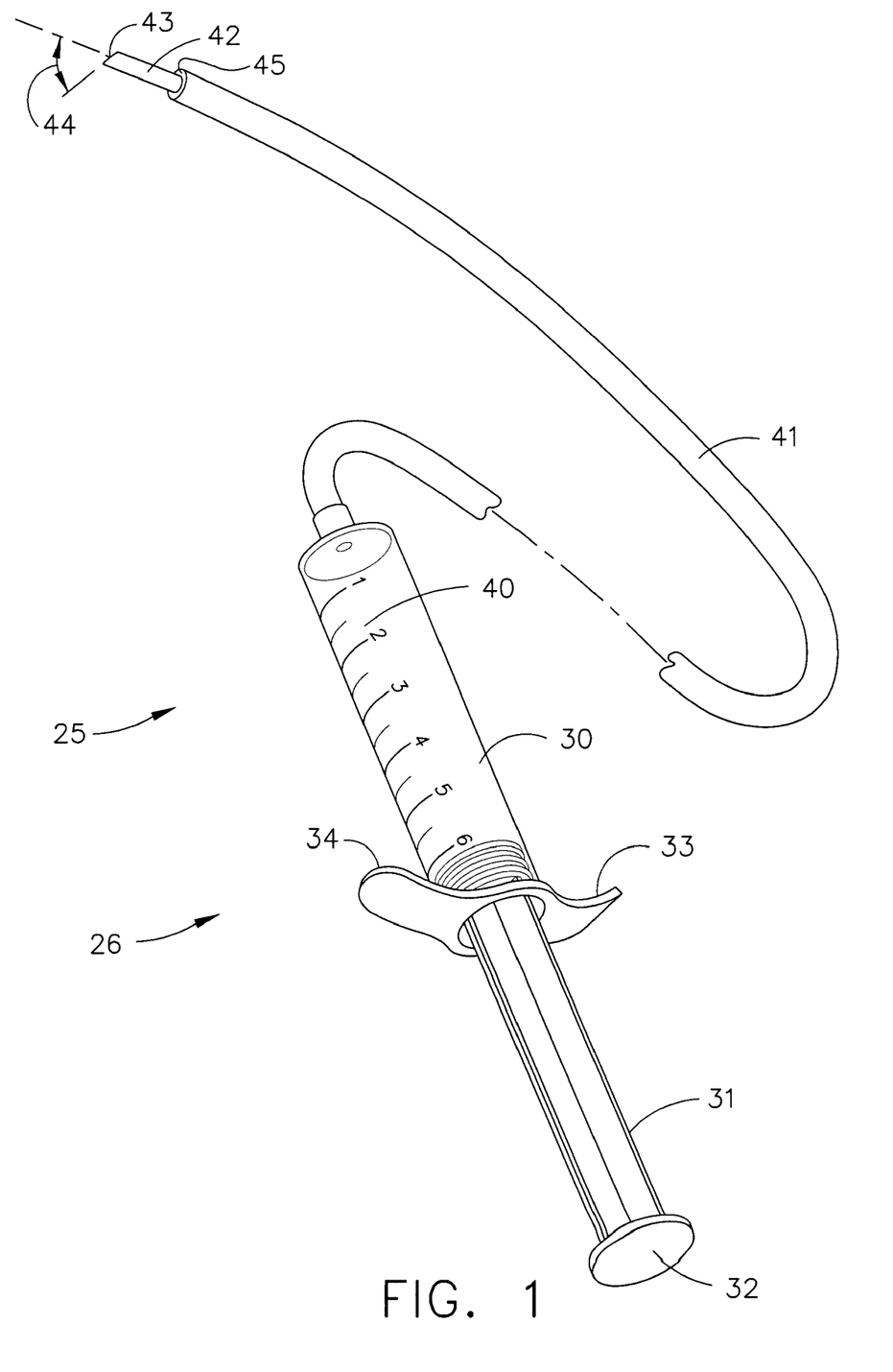
FIG. 1 is an isometric view of a medical device for applying a barrier material.

FIG. 1 illustrates an example of an apparatus or surgical device 25 that can place a barrier into or about an intestine. Surgical device 25 has a body 30 containing barrier material 40 that can be dispensed from body 30 with an actuation member 31. Body 30 and actuation member 31 together form a dispenser or pump 26 to dispense barrier material 40. Whereas a simple single chamber piston pump is shown, it would be obvious to one skilled in the art that the present invention could include a wide variety of pumps such as but not limited to a single or dual chamber pump, a piston pump, a motorized pump, a rotary pump, a diaphragm pump, a squeeze bladder or any one of a number of other pumping mechanisms Surgical device 25 also has grips 32, 33, and 34. A hose 41 could extend from body 30 so that the pump 26 can remain outside the patients body, and the hose can dispense barrier materials 40 into the patient. An applicator 42 can be attached to a distal end of hose 41 for passage of barrier material 40 therefrom during application to tissue. A sharp 43 may be placed on a distal end of applicator 42 to penetrate tissue, and can have an angle 44 to improve penetration and separation of tissue layers. Sharp 43 can be placed on applicator 42. A distal end of hose 41 is a stop 45 to limit depth of penetration of applicator 42 into tissue. To one skilled in the art, stop 45 can be any feature, such as a ring, on applicator 42. Also by way of example, stop 45 could also be adjustable to set the depth of penetration according to surgeon preference.

Barrier material 40 of the present invention prevents the passage of nutrients from the intestine and into the blood stream. For example, barrier material 40 can be non-permeable barrier or a partially permeable barrier to the passage or transfer of nutrients. Barrier material 40 could be a fluid, or a combination of fluids. As used herein, the term "fluid" comprises liquids, gases, gels, microparticles, and any other material which can be made to flow between a pressure gradient. Additionally, barrier material 40 may undergo a property or phase change within the patient from a fluid to a solid, or from a solid to a fluid or any state between fluid and solid. By way of example, the phase change could involve cross linking or polymerization.

One example of a barrier material 40 that undergoes a property change could be a polymerizable and/or cross-linkable material such as but not limited to a cyanoacrylate adhesive. The adhesive material, for example, may be but not limited to a monomeric (including prepolymeric) adhesive composition, a polymeric adhesive composition, or any other compound that can adhere to tissue and create a barrier to nutrient absorption. In embodiments, the monomer may be a 1,1-disubstituted ethylene monomer, e.g., an .alpha.-cyanoacrylate. When cross linked, the cyanoacrylate changes from a liquid to a solid barrier material 40a. Cross linked barrier material 40a can be a rigid or a flexible barrier and can be non-permeable or permeable. If desired, barrier material 40 can be a single part or dual part adhesive, and/or can contain additives 46. Other suitable single part and dual part adhesive barrier materials 40 and additives 46 may be found in United States Application 20040190975 by Goodman et al. which is herein incorporated by reference in it's entirety.

For example, additives 46 can be can included as either mixed into the barrier material 40 composition, or stored in a separate compartment from the barrier material 40 for mixing on demand at a later time. By way of example, some additives 46 can be pre-mixed and stored in the barrier material 40 if they do not react or degrade the barrier material 40. Other additives 46 that may react with the barrier material 40 can be stored in a separate compartment and mixed prior to or during application. Delivery of the barrier material 40 and additives 46 from separate compartments could be accomplished with a multiple chambered pump surgical device (not shown), or in multiple separate surgical devices 25. The separate materials could be mixed together outside the compartments, within the compartments, after leaving the compartments, after they are applied from the injector 42, or anywhere in between. A single passage, multiple passage, or multiple hose configuration could be used to deliver the materials to a single injector 42 or to multiple injectors 42.

Examples of suitable additives 46 include, but are not limited to, adhesion initiators, plasticizing agents, thixotropic agents, buffers, catalysts, fillers, micro particles, thickeners, solvents, drugs, medicaments, natural or synthetic rubbers, stabilizers, pH modifiers, bioactive agents, cross-linking agents, chain transfer agents, fibrous reinforcements, colorants, preservatives, formaldehyde reducing or scavenging agents, flavorants, perfumes, mixtures thereof, and the like. By way of example, an additive 46 comprising an adhesive initiator could be in one chamber of a device, and the barrier material 40 in a second chamber. One or more pumps 26 can be used to dispense additive 46 and barrier material 40 from injector 42 and the adhesive initiator would polymerize the mix of adhesive 40 and adhesive initiator.

The polymerizable and/or cross-linkable material may be neat (no additional compounds added) or thinned in a solvent, emulsion, or suspension. Suitable solvents, according to an example of this invention, include alcohol, ether alcohol, hydrocarbons, halogenated hydrocarbons, ethers, acetals, ketones, esters, acids, sulfur- or nitrogen-containing organic compounds, mixtures thereof and the like. A partial, but not a total list of other possible suitable solvents are disclosed in U.S. Pat. No. 5,130,369 to Hughes et al. and U.S. Pat. No. 5,216,096 to Hattori et al., the entire disclosures of which are incorporated herein by reference. These solvents may be used either independently, or in combination of two or more. They may also be used in conjunction with water to the extent that the polymerizable and/or cross-linkable material is dissolved or suspended in such a mixture. The total amount of solvent that may be incorporated into the polymerizable and/or cross-linkable material may be 0 to 99, preferably 1 to 50, and more preferably 3 to 25 percent by weight. Selection of the amount will, of course, depend on the desired monomer and process conditions, and amounts outside these ranges may be acceptable.

Exemplary additives 46 that are medicaments include, but are not limited to, quaternary ammonium halides such as benzalkonium chloride and benzethonium chloride; chlorhexidine sulfate; gentamicin sulfate; hydrogen peroxide; quinolone thioureas; silver salts, including, but not limited to, silver acetate, silver benzoate, silver carbonate, silver chloride, silver citrate, silver iodide, silver nitrate, and silver sulfate; sodium hypochlorite; salts of sulfadiazine, including, but not limited to silver, sodium, and zinc salts; and mixtures thereof. Preferable medicaments are those that are anions or help in radical generation or that are ion pairs or are themselves radicals.

In embodiments, the medicament is preferably a quaternary ammonium halide such as alkylbenzyldimethylammonium chloride (benzalkonium chloride; BAC) with an alkyl containing 6-18 carbon atoms, its pure components, or mixtures thereof, or benzethonium chloride; or a salt of sulfadiazine, such as a silver, sodium, or zinc salt.

The medicament can have a pharmaceutical effect only at the site of application (i.e., limited to the tissue on/in which it is applied), or it can have a systemic effect (by systemic, it is not only meant that the medicament has an effect throughout the patient's body, but also at a specific site other than the site of application). In embodiments where the medicament is applied in an amount sufficient to show a systemic pharmaceutical activity, it can be absorbed, transported, or otherwise distributed to the site or sites within the patient where the pharmaceutical activity is desired, e.g., through the cardiovascular or lymph systems. The medicament may be in the form of a solid, such as a powder or a solid film, or in the form of a liquid, such as a watery, viscous, or paste-like material. The medicament may also be compounded with a variety of additives, such as surfactants or emulsifiers, and vehicles.

In embodiments, the monomer composition and/or its packaging are preferably sterilized. Sterilization of the monomer composition and/or its packaging can be accomplished by techniques known to one of ordinary skill in the art, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation, as described in U.S. patent application Ser. No. 09/025,472, filed on Feb. 18, 1998, the entire disclosure of which is incorporated herein by reference. The composition must show low levels of toxicity to living tissue during its useful life. In preferred embodiments of this invention, the composition is sterilized to provide a Sterility Assurance Level (SAL) of at least 10-3. In embodiments, the Sterility Assurance Level may be at least 10-4, or may be at least 10-5, or may be at least 10-6. Further details of sterilization are disclosed in incorporated U.S. patent application Ser. No. 09/874,039.

Figure 2:
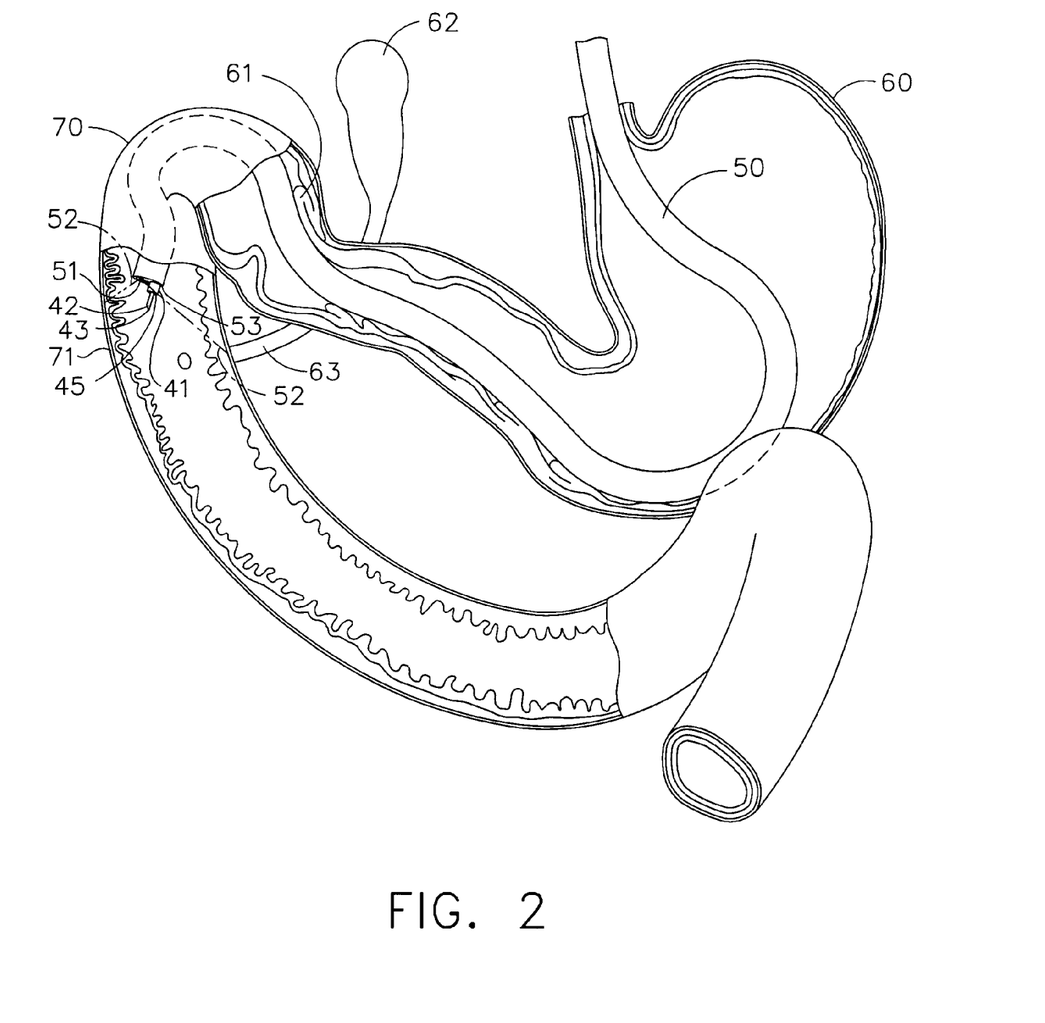
FIG. 2 is a partial cross sectional view showing an endoscope inserted into a patients stomach and small intestine and viewing a portion of the inner lumen of the small intestine prior to placing a barrier material into tissue of the small intestine with a portion of a surgical apparatus extending from the endoscope.

FIG. 2 shows an endoscope 50 inserted into a patient's stomach 60, through the pyloric valve 61 and partially into an upper section or duodenum 70 of a small intestine 71. Bile from gall bladder 62 enters the duodenum 70 through a cystic duct 63. In this view, the surgeon is using the endoscope optics 51 as indicated by the dashed lines 52 to view into the duodenum 70. Applicator tip 42 and hose 41 are shown just extending from a working passageway 53 in endoscope 50.

Figure 3:
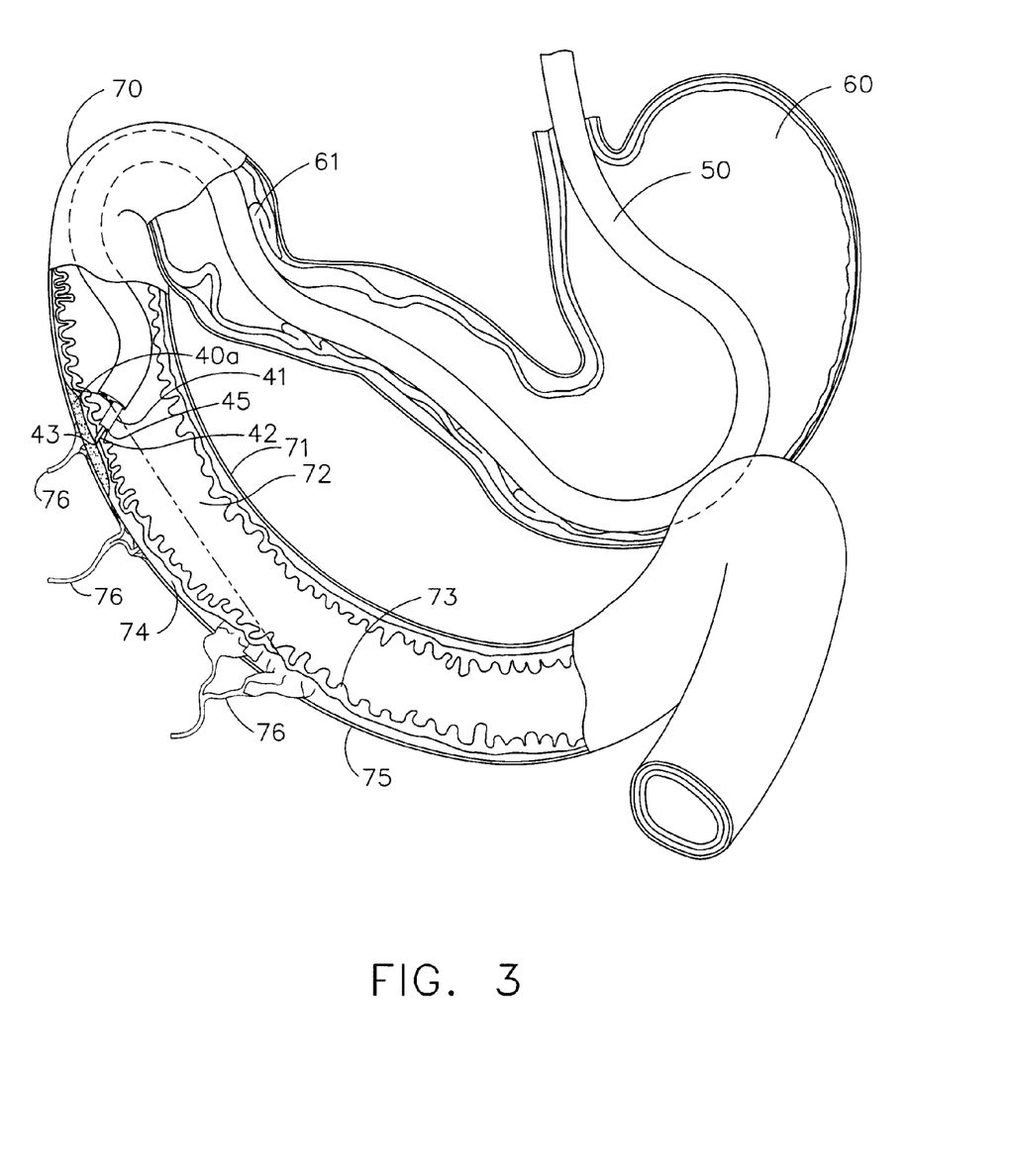
FIG. 3 is the partial cross sectional view of FIG. 2 with an additional portion of the small intestine removed to show structures and layers of the small intestine and the placement of a first injection of a barrier material between layers of the intestinal lumen with a surgical apparatus of the present invention.

By way of example, FIG. 3 shows a portion of the duodenum 70 of the small intestine 71 cross sectioned and removed to show the inner surface and layers of small intestine 71. The endoscope is positioned to look at a portion of the folds of inner lumen 72, and applicator 42 is inserted between layers of the duodenum 70. Angle 44 on applicator 42 has facilitated separation of the layers by lifting one of the layers up on the angled tip. Stop 45 is spaced away from a distal end 42a of applicator 42 and limits the depth of penetration to a desired depth. By way of example, stop 45 could be positioned to stop the distal tip 40a between two intestinal layers so that the barrier material 40 can be injected therebetween. By way of example, stop 45 could be attached to the applicator 42 or could be a distal end of hose 41 spaced from distal end 42a of applicator 42. Barrier material 40 is shown being injected interstitially as a fluid between mucosa 73 and muscle layers 75. This lifts middle layer mucosa 73 and inner layer submucosa 74 away from the outer muscular layer, creates a barrier of injected barrier material 40a therebetween and blocks the nutrient absorbing submucosa 74 and mucosa 73 from delivering nutrients to and vascular structure 76. By way of example, after injection, injected barrier material 40a can harden by polymerization and/or cross-linking by an adhesive initiator or moisture to form a hardened barrier 40b. Thus, injected barrier material 40a may undergo a change to a hardened barrier 40b to prevent nutrients from reaching the blood stream.

Figure 4:
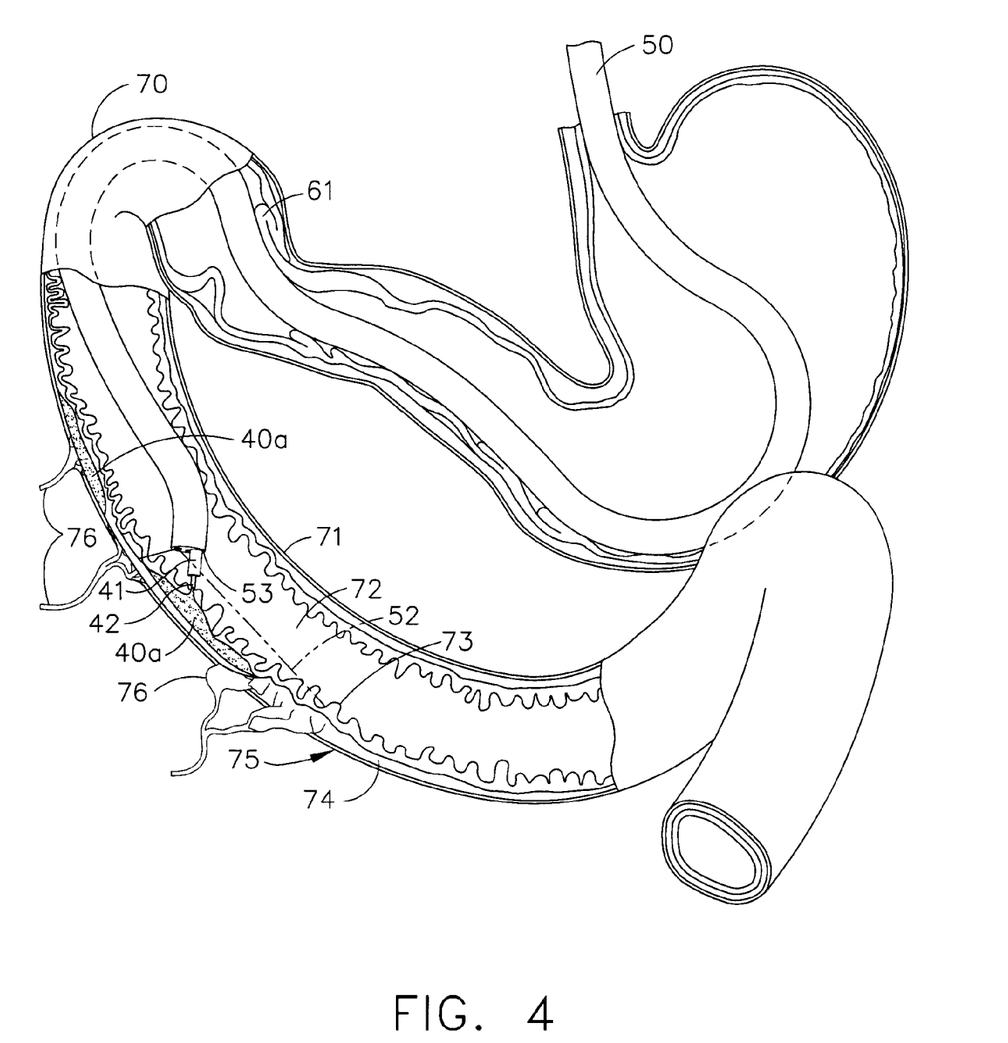
FIG. 4 is the partial cross sectional view of FIG. 3 showing a second placement of the barrier material at a second site along the intestinal lumen.

FIG. 4 shows the view of FIG. 3 with the endoscope 50 repositioned to a second surgical site for a second injection of barrier material 40. In this example, the surgeon has decided to inject the barrier material 40 between the inner submucosal layer 74 and the middle mucosal layer 73. This creates a second barrier of injected barrier material 40a that blocks nutrient flow to the vascular structure 76.

Figure 5:
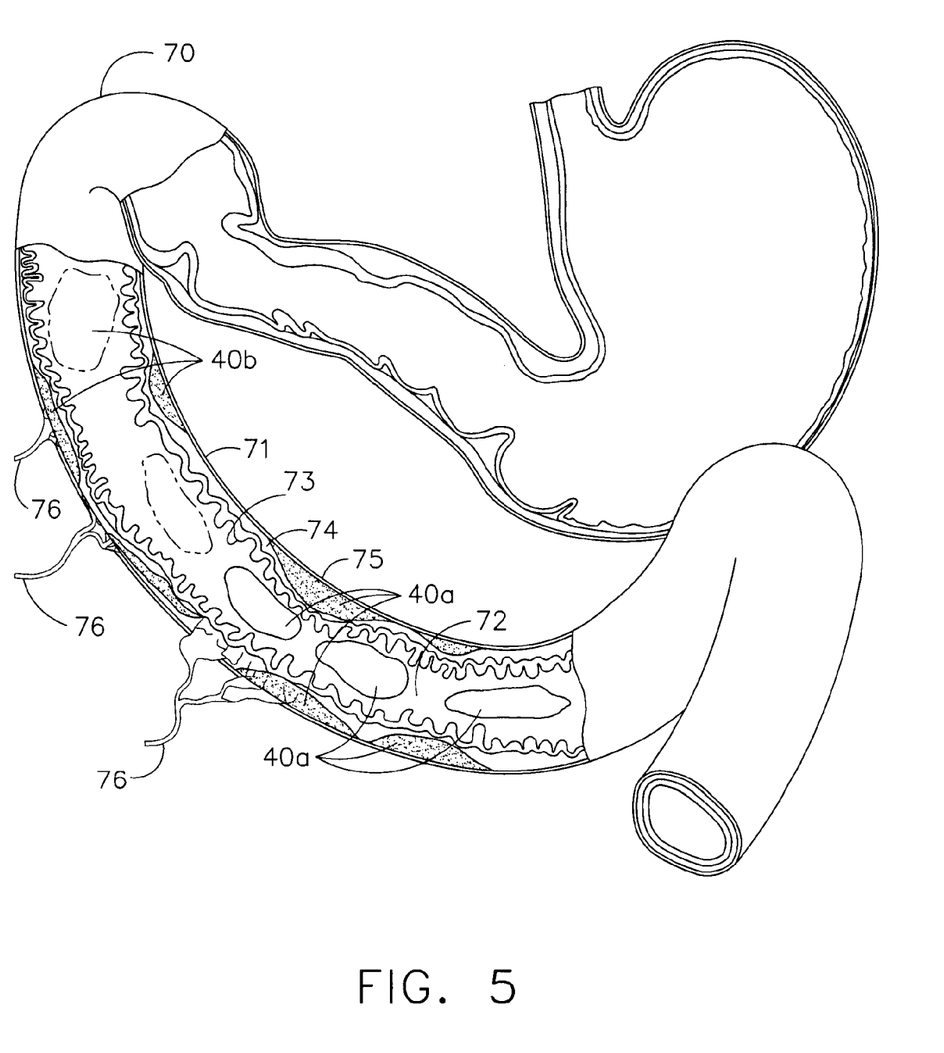
FIG. 5 is a the partial cross sectional view of FIG. 4 showing the intestinal lumen after placement of the barrier material at a plurality of sites along the small intestine.

FIG. 5 shows the duodenum of the patient after a plurality of injections of injected barrier material 40a along the length of duodenum 70. The plurality of injection sites has blocked a significant portion of the duodenum 70 from transferring nutrients to the vascular structures 76 resulting in reduced caloric absorption. The area of duodenum 70 with interstitial blockage can range from between 5 percent to 80 percent of the nutrient absorption area of the inner lumen 72 of duodenum 70. Injected barrier material 40b in the dashed line areas has hardened or polymerized to form a nutrient blocking barrier, and injected barrier material 40a is still fluid.

Figure 6:
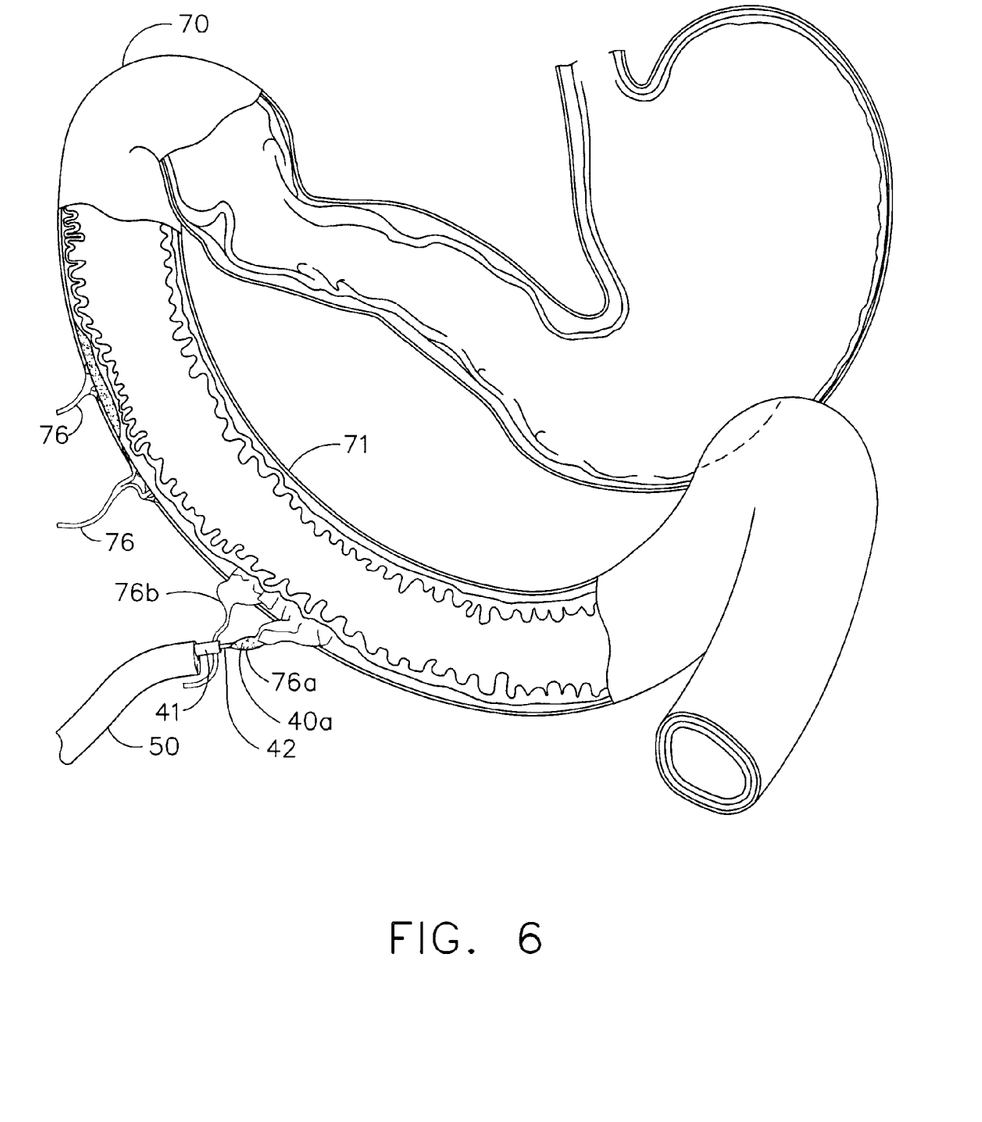
FIG. 6 is a partial cross section of the stomach and small intestines showing placement of a barrier material within a vascular structure supplying blood to the small intestine.

By way of example, FIG. 6 shows an alternate embodiment of using the barrier material 40 to reduce nutrient delivery from the intestines 71 to the vascular system. In this view, the endoscope is inserted into the abdominal area through an incision or a trocar and is shown injecting barrier material 40a into the vascular structure 76. The injected barrier material will block some percent of the vascular structure 76a resulting in reduced blood flow to the intestine 71 and decreased absorption of nutrients into the blood stream. As shown, vascular branch 76a is being occluded or blocked and vascular branch 76b remains unblocked. This technique could be used to selectively stop the flow of nutrients from a portion of intestine to the blood stream.

The use of barrier material 40 is not limited to endoscopic surgery (FIGS. 2-6) but can be applied to open procedures as well. In open procedures, the patient's abdomen is opened surgically enabling direct access to the intestinal areas. Surgical device 25 can be used to place barrier material 40 as described above, or hose 41 could be removed and applier 42 connected to the body 30 for placement of barrier material 40. Also by way of example, adhesives can be delivered to a surgical site without a pump such as a pen type device with a frangible adhesive ampoule like that disclosed in United States Application 20060049203 to E. Boone et al which is herein incorporated by reference in it's entirety, or the Dermabond® ProPen sold by Closure Medical Corporation, 5250 Greens Dairy Road Raleigh, N.C. 27616.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, whereas the above examples place adhesives between tissue layers or in vascular structures, to one skilled in the art, the invention is not just limited to these examples but can include any other means of using an adhesive to limit nutrient absorption such as placing the adhesive onto the inner surface of the duodenum to block nutrient absorption.

What is claimed is:

1. A method of using an applicator to place a barrier in a vascular structure proximate to a nutrient absorbing organ to achieve weight loss in a patient, wherein the vascular structure has a plurality of vascular branches, wherein the nutrient absorbing organ is a duodenum having an inner lumen, one or more inner layers of mucosal or submucosal tissue surrounding the lumen, and an outer muscular layer surrounding the inner layers, wherein the one or more inner layers have a smooth portion downstream from a pyloric valve and a folded portion downstream from the smooth portion, the inner layers being configured to absorb nutrients from contact with food and to transfer the nutrients to a patient's bloodstream through a network of connecting blood vessels, wherein the applicator has a tip configured to pierce the tissue of a vascular structure, wherein the tip comprises an angled surface for piercing tissue, the method comprising:
   a) placing the applicator into the tissue of the vascular structure located near the nutrient absorbing organ, wherein the applicator is inserted through the abdomen, wherein the abdomen is pierced using a trocar and the applicator is inserted through the trocar;
   b) piercing the tissue of the vascular structure located near the nutrient absorbing organ with the applicator tip without entering the inner lumen defined by the nutrient absorbing organ and without entering the mucosal tissue surrounding the lumen; and
   c) applying a polymerizable fluid barrier from the placed applicator tip to a selected portion of the plurality of vascular branches such that the polymerizable fluid barrier affects only the selected portion of the plurality of vascular branches such that the flow of nutrients from the nutrient absorbing organ through the selected portion of the plurality of vascular branches to the blood stream is stopped entirely for the selected portion of the plurality of vascular branches blocked by the polymerizable fluid barrier.

2. The method of claim 1 wherein the polymerizable fluid barrier is a polymer adhesive.

3. The method of claim 2 wherein the polymer adhesive is one or more polymer adhesives selected from the group consisting of:
   a) a polymerizable monomer,
   b) a polymerizable 1,1,1-disubstituted ethylene monomer, and
   c) a cyanoacrylate formulation.

4. The method of claim 3 further including the step of polymerizing the polymer adhesive in tissue.

5. The method of claim 1 wherein during the step of placing the applicator into tissue, the applicator is placed interstitially between layers of an intestine.

6. The method of claim 5 further including a step of moving the applicator to tissue at another site of the nutrient absorbing organ and repeating the steps of placing the applicator and applying the fluid barrier until between about 10 percent and about 80 percent of available nutrient flow is blocked by a plurality of fluid barriers placed at the plurality of surgical sites.

7. The method of claim 1 wherein the polymer is placed into a portion of a vascular tissue structure attached to the nutrient absorbing organ to absorb nutrients therefrom, wherein placing the barrier material into the vascular tissue structure reduces blood flow to nutrient absorbing organ and reduces the transfer of nutrients into the blood stream.

* * * * *